Figure 1:
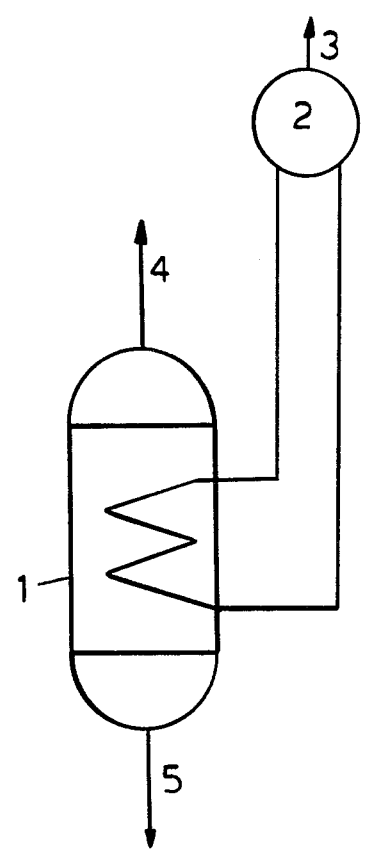

United States Patent [19]

Pagani

[11] 4,098,809
[45] Jul. 4, 1978

[54] PROCESS FOR THE PRODUCTION OF DIMETHYL ETHER

[75] Inventor: Giorgio Pagani, Milan, Italy

[73] Assignee: Snamprogetti S.p.A., Milan, Italy

[21] Appl. No.: 642,983

[22] Filed: Dec. 22, 1975

Related U.S. Application Data

[63] Continuation of Ser. No. 424,951, Dec. 17, 1973, abandoned.

[30] Foreign Application Priority Data

Dec. 20, 1972 [IT] Italy ............................... 33276 A/72

[51] Int. Cl.$^2$ ............................................. C07C 27/06
[52] U.S. Cl. ............................... 260/449 R; 260/449.5
[58] Field of Search ............ 260/449 R, 449.5, 614 R

[56] References Cited

U.S. PATENT DOCUMENTS 3,894,102   7/1975   Chang et al. ...................... 260/449.5

OTHER PUBLICATIONS

Brown et al., "Industrial & Engineering Chem," vol. 21, No. 4 (1929), pp. 310–313.
Ipatieff, "Journal of the Amer. Chem. Soc.," vol. 67, (1945), pp. 2168–2172.

*Primary Examiner*—A. Siegel
*Attorney, Agent, or Firm*—Morgan, Finnegan, Pine, Foley & Lee

[57] ABSTRACT

Dimethyl ether is prepared by feeding a mixture of CO, $CO_2$ and $H_2$, wherein the quantity of CO is in excess of the stoichiometric value, to a reactor containing a methyl alcohol synthesis catalyst, such as a copper base or chrome-zinc base catalyst, and a methyl alcohol dehydration catalyst, such as alumina, whereby methyl alcohol is formed as an intermediate product which is transformed into dimethyl ether in the same reactor at a temperature in the range of 220° to 400° C and a pressure in the range of 30 to 500 kg/cm$^2$.

4 Claims, 1 Drawing Figure

PROCESS FOR THE PRODUCTION OF DIMETHYL ETHER

This is a continuation, division of application Ser. No. 424,951 filed Dec. 17, 1973 now abandoned.

The present invention relates to a process for the production of dimethyl ether (DME).

More particularly the present invention relates to a process for the production of dimethyl ether via methyl alcohol.

Dimethyl ether could be produced by a Fischer-Tropsch type reaction through a direct synthesis from CO and $H_2$ according to the reaction $$2CO + 4H_2 \rightleftarrows CH_3 - O - CH_3 + H_2O$$

but the amount of by-products would be extremely high since there is no selective catalyst adapted to carry out the reaction exclusively in that way.

Therefore if dimethyl ether were produced according to the cited reaction it would then be necessary to separate said dimethyl-ether from all formed by-products; this, besides rendering the process complicated, would require expensive apparatus and high operating costs.

It has been surprisingly found that it is possible to produce dimethyl ether in a selective way, avoiding the drawbacks which would be present if use were made of the aforesaid reaction.

The subject of the present invention is a process for producing dimethyl-ether starting from CO, $CO_2$ and $H_2$ with an intermediate production of methyl alcohol and its dehydration to dimethyl-ether directly in the same reactor. The process of the present invention comprises feeding to a synthesis reactor substantially CO, $CO_2$ and $H_2$ and reacting them in the presence of a catalyst for the methyl alcohol synthesis, in particular a copper base catalyst, on a carrier active in to the dehydration of methyl alcohol, in particular alumina, at a temperature in the range of from 220° C to 320° C.

Alternatively the reaction can be carried out in the presence of a catalyst for the synthesis of methyl alcohol based on zinc and chrome on a carrier active in the dehydration of methyl alcohol of the above described type at a temperature in the range of from 280° to 400° C.

The catalyst for the methyl alcohol synthesis could be also simply mixed with a catalyst for the dehydration of methyl alcohol.

Moreover the catalyst can be placed in layers in the reactor, alternatively layers of catalyst for the methyl alcohol synthesis and layers of catalyst for dehydrating methyl alcohol.

As regards the reaction pressure it can range between 30 and 500 kg/cm². By working in this way it is possible to increase in a remarkable way the conversion rate of CO, $CO_2$ and $H_2$ in the reactor, since most of the synthesis methyl alcohol, as soon as it forms, is dehydrated to DME and the catalyst bed operates always in the presence of low methyl alcohol concentrations. This fact makes it possible to transform most of the gases fed to the reactor into DME plus a certain percentage of residual methyl alcohol, keeping at very low values the unreacted gas which has to be recycled to the reactor, with economies and operating advantages which can be readily appreciated.

Let us examine now in detail the mechanism of the chemical reactions which occur:

$$CO + 2H_2 \rightleftarrows CH_3OH \quad \quad 1$$

$$2CO + 4H_2 \rightleftarrows CH_3-O-CH_3 + H_2O \quad \quad 2$$

$$H_2O + CO \rightleftarrows CO_2 + H_2 \quad \quad 3$$

$$CO_2 + 3H_2 \rightleftarrows CH_3OH + H_2O \quad \quad 4$$

$$2CH_3OH \rightleftarrows CH_3-O-CH_3 + H_2O \quad \quad 5$$

Of these equations the one numbered (2) is a linear consequence of reactions numbered (5) and (1) and the one numbered (4) depends on reactions numbered 3 and 1.

Reactions occurring in our reactor can therefore be described by the following chemical equations:

$$CO + 2H_2 \rightleftarrows CH_3OH$$

$$CO + H_2O \rightleftarrows CO_2 + H_2$$

$$2CH_3OH \rightleftarrows CH_3-O-CH_3 + H_2O$$

Even if the dehydration reaction of methyl alcohol is thermodynamically more favoured than the one of the methyl alcohol synthesis, the presence of water in the reacted gas does not allow a high dehydration of methyl alcohol and after all holds down the percentage of transformation of fresh gas into DME per passage through the reactor.

By using a synthesis gas relatively rich in $CO_2$ (for instance the one produced by steam reforming of light hydrocarbons in which gas the amount of $CO_2$ is of the same order of magnitude as that of CO) with respect to the dehydration water one has to add water relative to the conversion of $CO_2$ to CO according to reaction (3) and the yields through trasformation into DME per passage are lowered still more.

All this does not occur if one operates with a CO rich gas, having low $CO_2$ percentages, which gas can be obtained for instance, by partial combustion of more or less heavy hydrocarbons and by coal gasification, wherein the amount of CO present is in substantial excess with respect to the stoichiometric amount necessary for the methyl alcohol synthesis.

By working with such a gas, the dehydration water, as soon as it forms, is consumed by the excess CO (thus producing $CO_2$ + $H_2$) and consequently the methyl alcohol dehydration reaction and the synthesis reactions connected to the dehydration reaction go on up to a very high conversion (up to 80% for instance per passage through the reactor).

The following qualitative example will clarify that important concept. Suppose one starts with a gas having a $H_2$/CO ratio lower than 2, i.e. lower than the value required for producing methyl alcohol. In accordance with the conventional technique, it would be necessary to convert the excess of CO with steam to $CO_2$ and $H_2$ the excess of CO and to eliminate the produced $CO_2$.

By working according to the process of our invention, however, the synthesis gas composition does not need to be adjusted because the conversion of CO to $CO_2$ and $H_2$ will take place directly in the synthesis reactor (in fact the copper or chrome-zinc base catalysts are extremely active in the water gas reaction CO + $H_2O$ = $CO_2$ + $H_2$) by consuming the dehydration water as soon as it forms thus providing very high yields per passage through the catalytic bed.

As a limit, when CO is in substantial excess in comparison with hydrogen, the single dehydration water alone may not be sufficient to guarantee a good CO conversion and therefore it will be useful to add some steam.

It is to be observed that if the methyl alcohol synthesis is effected in a first reactor and then the dehydration to dimethyl-ether of the produced methyl alcohol is carried out in a second reactor the methyl alcohol synthesis plant would be of conventional type and therein the conversion would be very low (10–15%) and consequently the recycles and costs would be high and the plant for dehydrating methyl alcohol to dimethyl-ether would require a heat consumption for vaporizing methyl alcohol, a rectification of the product and a recycle of the unconverted methyl alcohol.

It is obvious that with such a scheme the dimethyl-ether cost will be higher than the methyl alcohol cost.

In our case on the contrary the dimethyl-ether cost is even lower than the cost of methyl alcohol produced according to the conventional techniques owing to the great plant simplicity.

The process which is the subject of the present invention makes it possible therefore to obtain dimethyl-ether starting from CO, $CO_2$ and $H_2$ with a very high selectivity and a very low cost.

The use of such dimethyl-ether could be as of fuel for domestic and industrial uses specially now that the energy sources are rapidly getting exhausted.

At present because of the scarcity of the energy sources in the places where energy is consumed, besides the production of synthetic methane (SNG) by using coarse fuels such as heavy oils, pit-coal and so on, the use of natural gas produced in fields also very far from the utilization places is of interest.

For transporting the natural gas use is made, when possible, of methane pipe lines.

When for the transport it is necessary to cross very large seas, the transport technique via methane pipe-line is no longer possible and usually the liquefaction technique is used; the natural gas is liquefied in proximity to the loading port and transported by means of special tankers.

The liquefied natural gas (GNL) is vaporized at the port of discharge and is introduced in the normal methane pipe-line network.

Recently the possibility of chemically transforming the natural gas into a liquid fuel for more easy transport has been considered. In particular the possibility of producing methyl alcohol and transporting the same by conventional tankers has been examined.

Given the low transformation yield of methane into methyl alcohol (about 50–60%) it is obvious that this system could be convenient only for low costs of the natural gas at the origin and for very long routes which make the transport of GNL expensive.

The utilization of methyl alcohol as a fuel, apart from the transformation and transport costs, involves in any case some problems connected essentially to:
- low heat value (the net heat value is ~5000 kcal/kg)
- high vapour pressure (it boils at 64.7° C) and consequently aptitude to form explosive mixtures
- toxicity Just because of these problems it is evident that methyl alcohol will be used as a fuel only for big uses as, for instances, the thermoelectric power plants.

If its utilization field as a fuel is to be amplified, it will be necessary to go on with a further chemical transformation of methyl alcohol. One of such possibilities could be the transformation of methyl alcohol again into methane:

$$CH_3OH + H_2 = CH_4 + H_2O;$$

the hydrogen necessary for the transformation could be produced by decomposition of a portion of methyl alcohol, converting CO and removing $CO_2$:

$$CH_3OH = CO + 2H_2$$

$$CO + H_2O = CO_2 + H_2$$

As a whole the operation can be represented in the following way:

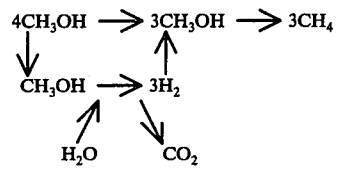

The energy efficiency of the transformation based on the heat values is equal to about 90%, aside from the possible consumption of thermal energy for the process.

The advantage of this cycle would be that methane could be directly introduced into the methane pipe-line network, but the drawback would be the re-transformation operation cost which would be added to the one, already high, of the first transformation and of the transport.

By the process which is the subject of the present invention we have overcome the drawbacks and problems connected with the use of methyl alcohol and its possible transformation into $CH_4$ or DME obtaining at low costs a product (DME) which is up to traditional fuels.

In fact the characteristics of DME as a fuel are more interesting than those of methyl alcohol, both because it is in gaseous state, and because, owing to the loss of water, it has a higher heat value:
- net heat value: 6940 kcal/kg 1 (14,250 kcal/Nm³)
- boiling temperature: −27° C
- vapor pressure at 25° C: 6 kg/cm² absolute
- no toxicity.

Its characteristics are therefore similar to those of a gas of liquified oil (GPL) even though it has a lower heat value.

It is possible to foresee a remarkably wider field of uses of methyl alcohol, since it can be utilized for each use type (as a sustitute of GPL, of town gas and for industrial uses).

It will be possible also to introduce, under appropriate conditions, DME into the methane pipe-line network.

The high conversions, obtainable in a reactor for the contemporaneous synthesis and dehydration of methyl alcohol, will appear from the following examples which, obviously have no restrictive purpose.

We make reference to FIG. 1 in which there is schematized, for sake of simplicity, only the synthesis reactor (1) which is of isothermal type with removal of the reaction heat through (2) for producing steam (3). The raw gas is fed through (4) and the reaction products are discharged through (5).

EXAMPLE 1

The gas to be transformed, available at a pressure of 100 kg/cm$^2$ and a temperature of about 250° C, was fed to the reactor wherein the methyl alcohol synthesis reaction and the reaction of dehydration of methyl alcohol contemporaneaously occur in accordance with the described process.

The characteristics of the feed gas, obtained by the known process of partial oxidation of methane with O$_2$ are:

| | |
|---|---|
| flow rate | 100.000 Nm$^3$/h |
| composition: | |
| H$_2$ | 62.67% b.v. |
| CO | 35.20% b.v. |
| CO$_2$ | 1.46% b.v. |
| CH$_4$ | 0.37% b.v. |
| N$_2$ | 0.30% b.v. |
| | 100.00% b.v. |
| temperature | 250° C |
| pressure | 100 kg/cm$^2$ |
| catalyst: Cu/Zn/Cr with an atomic ratio equal to 82/16/4, the carrier being alumina. | |

The reacted gas leaving the reactor had the following characteristics:

| | |
|---|---|
| flow rate | 56,000 Nm$^3$/h |
| composition: | |
| H$_2$ | 48.58% b.v. |
| CO | 8.45% b.v. |
| CO$_2$ | 17.75% b.v. |
| CH$_4$ | 0.66% b.v. |
| N$_2$ | 0.53% b.v. |
| CH$_3$OH | 2.23% b.v. |
| CH$_3$OCH$_3$ | 18.48% b.v. |
| H$_2$O | 3.32% b.v. |
| | 100.00% b.v. |
| temperature | 270° C |

We obtained therefore a production of 1,250 Nm$^3$/h of methyl alcohol and 10,360 Nm$^3$/h of DME.

This means that the conversion per passage based on the present CO + H$_2$ is 67%.

EXAMPLE 2

The characteristics of the feed gas, obtained by the process of partial oxidation with O$_2$ of a heavy oil are:

| | |
|---|---|
| flow rate | 100,000 Nm$^3$/h |
| composition: | |
| H$_2$ | 44.70% b.v. |
| CO | 51.90% b.v. |
| CO$_2$ | 1.78% b.v. |
| CH$_4$ | 0.27% b.v. |
| N$_2$ | 1.35% b.v. |
| | 100.00% b.v. |
| temperature | 250° C |
| catalyst: the same as in example 1. | |

The reacted gas leaving the reactor had the following characteristics:

| | |
|---|---|
| flow rate | 50,350 Nm$^3$/h |
| composition: | |
| H$_2$ | 14.05% b.v. |
| CO | 29.97% b.v. |
| CO$_2$ | 27.30% b.v. |
| CH$_3$OH | 0.91% b.v. |
| CH$_3$OCH$_3$ | 24.20% b.v. |
| CH$_4$ | 0.54% b.v. |
| N$_2$ | 2.62% b.v. |
| H$_2$O | 0.41% b.v. |
| | 100.00% b.v. |
| temperature | 270° C |

We produced 460 Nm$^3$/h of CH$_3$OH and 12,150 Nm$^3$/h of DME. This corresponds to a transformation of entering CO + H$_2$ equal to 77%. With respect to the preceding case, because of the higher excess of CO, there is a higher total yield and also a higher methyl alcohol dehydration. The above conversion values appear very high when compared with the values obtainable with conventional processes for the methyl alcohol synthesis, wherein conversion per passage are in the the range of from 10 to 15%. The remarkable advantages obtainable in a plant working according to the present process are therefore obvious.

In the case described in example 1 concerning the transformation of methane into a more liquefiable and transportable fuel, the complete synthesis cycle can be constituted by a first reactor with a high yield (67%) wherein most of DME is produced; subsequently, after separation of DME + residual methyl alcohol and of excess CO$_2$, which in this case is not high, the residual gas can be fed to a second reactor, always for the synthesis and dehydration of methyl alcohol, for further conversion.

In the case described in example 2 concerning the transformation of heavy oil into DME, because of the high CO$_2$ excess, it will be convenient to work in another way and to transform most of the feed (77%) in a first reactor and, after separation of the produced DME + methyl alcohol, to feed the remaining gaseous mixture to a second reactor, possibly working at a higher pressure, in order to further transform into DME + methyl alcohol the CO + H$_2$ still present, without eliminating the formed CO$_2$.

It is possible to foresee that the obtained total conversion may be 90%. The residual gas, after separation of the products, can be vented or used as a burning gas having low heat value.

Since the dehydration water is consumed as soon as it forms, we obtain a product very concentrated in DME (95–96% by weight) which product can also be used without any rectification operation.

There will be therefore no need to provide expensive plants for CO conversion and for decarbonation and, possibly, for rectification. The process according to the invention is therefore important not only for transforming the natural gas into a fuel which is more easily liquefiable and transportable, but, more particularly, for transforming into a more valued form, such as DME is, coarse fuels such as heavy oils, pit-coal and so on, in competition with the processes for the production of synthesis natural gas.

What I claim is:

1. A process for the production of dimethyl ether in high yield wherein a feed mixture constituted by CO, CO$_2$ and H$_2$, in which the quantity of CO is in effective excess of the stoichiometric value, is reacted in a reaction zone in the temperature range of 220° C to 320° C and the pressure range of 30 to 500 kg/cm$^2$ over a Cu/Zn/Cr methyl alcohol synthesis catalyst having a carrier of alumina which is a methyl alcohol dehydration catalyst, so that methyl alcohol is formed as an intermediate which is then dehydrated into dimethyl ether in the same reaction zone.

2. Process as claimed in claim 1, wherein the reaction zone is constituted by alternate layers of said Cu/Zn/Cr catalyst for the methyl alcohol synthesis and said alumina catalyst for the methyl alcohol dehydration.

3. Process as claimed in claim 1, wherein the reaction zone is constituted by a mixture of the methyl alcohol synthesis catalyst consisting of Cu/Zn/Cr and of the methyl alcohol dehydration catalyst consisting of alumina.

4. Process as claimed in claim 1 wherein the mixture of the feed gases is the product of the partial oxidation of hydrocarbons.

* * * * *